(12) United States Patent
Plaβky et al.

(10) Patent No.: US 8,715,296 B2
(45) Date of Patent: May 6, 2014

(54) ADJUSTABLE TRACKING REFERENCE COMPRISING A CURABLE BONDING CONNECTION

(75) Inventors: Norman Plaβky, Erfurt (DE); Manuel Millahn, München (DE)

(73) Assignee: Brainlab AG, Feldkirchen (DE)

( * ) Notice: Subject to any disclaimer, the term of this patent is extended or adjusted under 35 U.S.C. 154(b) by 1040 days.

(21) Appl. No.: 12/394,130

(22) Filed: Feb. 27, 2009

(65) Prior Publication Data

US 2009/0227865 A1     Sep. 10, 2009

Related U.S. Application Data

(60) Provisional application No. 61/033,820, filed on Mar. 5, 2008.

(30) Foreign Application Priority Data

Feb. 28, 2008   (EP) ..................................... 08152071

(51) Int. Cl.
*A61B 19/00* (2006.01)
(52) U.S. Cl.
USPC .......................................... 606/130

(58) Field of Classification Search
USPC .......................... 606/86, 99, 130; 403/52–166
See application file for complete search history.

(56) References Cited

U.S. PATENT DOCUMENTS

| 4,548,581 A  * | 10/1985 | Huffman .......................... 433/64 |
| 6,666,870 B2 * | 12/2003 | Dixon et al. ..................... 606/76 |
| 2004/0068263 A1 | 4/2004 | Chouinard et al. |
| 2005/0124988 A1 | 6/2005 | Terrill-Grisoni et al. |
| 2006/0015119 A1 | 1/2006 | Plaβky et al. |

FOREIGN PATENT DOCUMENTS

| EP | 0 911 668 | 4/1999 |
| EP | 1 563 799 | 8/2005 |
| WO | 91 15154 | 10/1991 |

* cited by examiner

*Primary Examiner* — Katherine Dowe
*Assistant Examiner* — Michael Medoza
(74) *Attorney, Agent, or Firm* — Tucker Ellis LLP

(57) ABSTRACT

The invention relates to a medical tracking reference, comprising a fastening arm and a reference array holding arm to which a reference array is or can be attached, and comprising a joint between the arms which can be fixed using a fixing array, wherein the fixing array of the joint comprises a bonding connection which can be fixed using a curable bonding agent. It also relates to a method for setting the alignment of a medical tracking reference.

24 Claims, 3 Drawing Sheets

ADJUSTABLE TRACKING REFERENCE COMPRISING A CURABLE BONDING CONNECTION

RELATED APPLICATION DATA

This application claims the priority of U.S. Provisional Application No. 61/033,820, filed on Mar. 5, 2008, which is hereby incorporated in its entirety by reference.

FIELD OF THE INVENTION

The invention relates to an adjustable medical tracking reference and a method for setting the alignment of such a tracking reference.

BACKGROUND OF THE INVENTION

Such medical tracking references are used to determine the spatial position of objects by means of a medical tracking system which is assigned to a medical navigation system, wherein the tracking reference is fastened to such an object. An adjustable tracking reference comprising a joint, wherein a medical tracking reference comprises a fastening arm and a reference array holding arm to which a reference array is or can be attached and comprises a joint between the arms which can be fixed using a fixing array, is known from EP 1 563 799 A1. The tracking reference comprises a fastening arm via which it is fastened to the object, and a reference array holding arm to which the reference array is or can be attached, which in turn can be localized by the tracking system. A joint is situated between these two arms and serves to enable the reference array to also be arranged differently for different applications or different operating theatre setups, such that it can be detected by the tracking system in any event.

In accordance with the prior art, the joints are for example fitted with fixing screws, i.e. they can be made movable before the reference array holding arm is correctly aligned. However, the joints then have to be fixed again and remain fixed (using the setting screw), in order for navigation and tracking to be able to function.

However, it often occurs that the surgeons performing the treatment do not tighten or do not correctly tighten these fixing screws or setting screws, and that the joint therefore becomes loose again and the reference array moves during the treatment. This completely invalidates the registration, and navigation would lead to incorrect results.

SUMMARY OF THE INVENTION

It is the object of the present invention to propose a medical tracking reference and a method for setting the same, which avoids unintentional subsequent adjustments and associated tracking and/or navigation errors.

This object is solved by: a medical tracking reference comprising a fastening arm and a reference array holding arm to which a reference array is or can be attached, and comprising a joint between the arms which can be fixed using a fixing array, wherein the fixing array of the joint comprises a bonding connection which can be fixed using a curable bonding agent; and by a method for setting the alignment of a medical tracking reference comprising a fastening arm and a reference array holding arm to which a reference array is or can be attached, and comprising a joint between the arms which can be fixed using a fixing array, wherein the fixing array of the joint is fixed using a curable bonding agent which establishes a bonding connection. The sub-claims define preferred embodiments of the invention.

The tracking reference in accordance with the invention has a fixing array for the joint, comprising a bonding connection which can be fixed using a curable bonding agent. The term "bonding agent" here includes all liquids or solids which transition from a non-fixed state to a fixed state, thereby fixing elements in their vicinity relative to each other, wherein it is unimportant whether the transition is physically or chemically initiated and/or assisted, i.e. in other words, the invention lies in the fact that the two arms of the reference are fixed relative to each other, using a connecting technique which does not immediately allow the connection to be released but rather maintains the connection. Thus, while the joint fixed in this way can initially be easily set correctly, there is however no danger of a placement, once fixed, being incorrectly fastened or able to be released again. The cured bonding agent fixes the placement of the arms relative to each other—inadvertent adjustments can no longer occur. Tracking and navigation are secure and reliable.

In one embodiment of the present invention, a bonding space—in particular, a bonding gap—is provided in and/or on the joint, between the ends of the arms, which accommodates the curing bonding agent and in which the ends of the arms are fixed relative to each other. This enables the location at which the bonding agent is to be cured to be correctly set and verified, and the selected placement is reliably retained.

In one variant of the invention, the bonding space can be filled with a bonding agent which can be cured by an external influence, in particular by introducing a chemical substance or by applying energy from without, especially in the form of heating and/or cooling energy, sonic energy, electromagnetic radiation energy or light energy.

A tracking reference in accordance with the invention can comprise a container in or adjacent to the bonding space, which comprises the bonding agent and can be opened and/or destroyed by an influence on the joint from without, in particular by a relative movement of the arms, such that the bonding agent enters the bonding space, where it cures. In a second, preferably provided function, such a container—which can be an easily destructible glass or plastic container—can also serve, in its unopened and/or non-destroyed state, to couple the ends of the arms to each other in the joint and to hold them relative to each other in an initial placement. The strength of the container would then be selected such that, while it can be directly destroyed by the movement of the arms, this destruction would however be opposed by a large enough force that the "starting placement" of the arms relative to each other can be maintained while the reference is being routinely handled.

The bonding agent can be a one-component agent, in particular a one-component glue, which cures in the bonding space after a predetermined period of time. In accordance with another embodiment, the bonding agent is a multiple-component agent, in particular a multiple-component glue, which cures after a predetermined period of time due to contact between the components, wherein one of the components is in particular accommodated in the aforesaid container and another component is accommodated in the bonding space.

The strength of the bonding connection has to be great enough that it prevents an adjustment of the angle of the joint during the operation. This does not, however, mean that curing and/or fixing have to be irrevocable. It is possible to use a replastifiable agent as the bonding agent, especially one which can be re-liquefied by an external influence, in particular by introducing a chemical substance or by applying energy from without, for example in the form of heating and/or cooling energy, sonic energy, electromagnetic radiation energy or light energy. This is in particular useful when the tracking reference is designed as a reusable reference, wherein the bonding agent is made from a material whose hardening and softening capabilities cannot be impaired at sterilization temperatures, in particular above 100° C.

In another embodiment, however, the tracking reference in accordance with the invention is designed as a disposable reference, wherein the arms and the joint are in particular made from a plastic material and/or the bonding agent is made from a material which irretrievably loses its strength and/or solidity at sterilization temperatures, in particular above 100° C. Such a reference cannot be reused.

The joint can comprise a flexible sleeve which ends at the arms and seals them, and which prevents the bonding agent from escaping from the joint.

The method in accordance with the invention, mentioned at the beginning, can be characterized by the use of a reference comprising the features such as have been individually mentioned above, i.e. the particularity of the features of the disclosed devices also determines the execution of the method steps.

Put slightly differently, the present invention may also be characterized as follows: it provides a mechanism which allows the reference to be pre-operatively set but does not allow it to move intra-operatively, and it can be used for all mechanisms which first require an initial setting in the medical field and then a fixed position, as also for example in the case of the joints for a setting device of a bone cutting block.

In a first state, the joints to be set are rigid but can easily be "broken", for example by rotating the joint. Once the joint has been opened, the surgeon has a predetermined period of time in which to move the reference star (reference array) into the correct position, and the joint then cures and does not allow any subsequent unintentional movement. The different embodiments can be classified according to reusability criteria, or also for example according to criteria for the bonding agent (type of glue, one-component or multiple-component glue). A two-component glue would be mixed when the joint was "opened", i.e. moved for the first time, and would then cure. A one-component glue will fill the joint gap once "opened", cure after a short period of time and so fix the joint.

Reusable tracking references would allow the joint, once cured, to be re-released and set again. The surgeon can then predetermine the alignment of the reference array holding arm, in accordance with his personal operating theatre setup, since for the same surgeon, this will be similar for similar surgical incisions or even for other surgical incisions. Once the joint is fixed, a surgeon has his own version, adapted to himself, which saves time and avoids readjustments. In such cases, a glue and/or bonding agent is used which can withstand sterilization temperatures, and especially in the case of reusable references, the surgeon also has the option of subsequently resetting the alignment. As described above, the joint can then be released in different ways, and one such way which keeps the requirement for different instruments in the operating theatre small is to use a so-called HF knife, which is provided in most operating theatres anyway. This HF knife is used as an energy provider, in order to re-release and reset joints which have already been solidified and/or fixed. An ultrasound emitter can be used in the same way.

In principle, the energy of such devices which are provided in the operating theatre anyway can even be used beforehand to cure joints. The joints could then simply be filled with a bonding agent which cures when for example HF radiation or ultrasound waves are applied.

With regard to the possibility of providing the tracking reference as a disposable item, the entire unit can then be made of plastic, and reference markers which are to be fastened to the reference array holding arm are in most cases provided as disposable items anyway. Once used, the joint should not be able to be used again, and one safety feature is therefore that the glue is destroyed during any attempt at steam sterilization and the joint is thus loosened. It is then no longer able to be fixed, and is prevented from being used a second time. Using plastic materials makes the overall array very light, which in turn reduces the risk of it releasing intra-operatively. In addition, the entire reference can be radiolucent, which is advantageous for specific applications (fluoroscopy).

Suitable materials for the bonding agent or in particular glue include monomers, polymers, bone cement, ceramics ($Al_2O_3$, $TiO_2$), metal powder (Ti) and glass ($SiO_2$), and mixtures of these components with monomers and polymers (ceramics, metal powder and glass are not glues in their own right), and curing techniques—or as applicable also releasing techniques—which may generally be considered include ultrasound waves, thermal energy, infrared radiation, microwaves, UV radiation and electromagnetic radiation, wherein both the aforementioned lists are not to be interpreted as exhaustive. With regard to liquefying and solidifying materials, reference is made here to European patent application No. 07 122 134.5, the corresponding content of which is incorporated here by reference.

BRIEF DESCRIPTION OF THE DRAWINGS

The invention is illustrated below in more detail on the basis of example embodiments and by referring to the enclosed drawings. It can include any of the features described here, individually and in any expedient combination. In the enclosed drawings.

DETAILED DESCRIPTION

Figure 1:
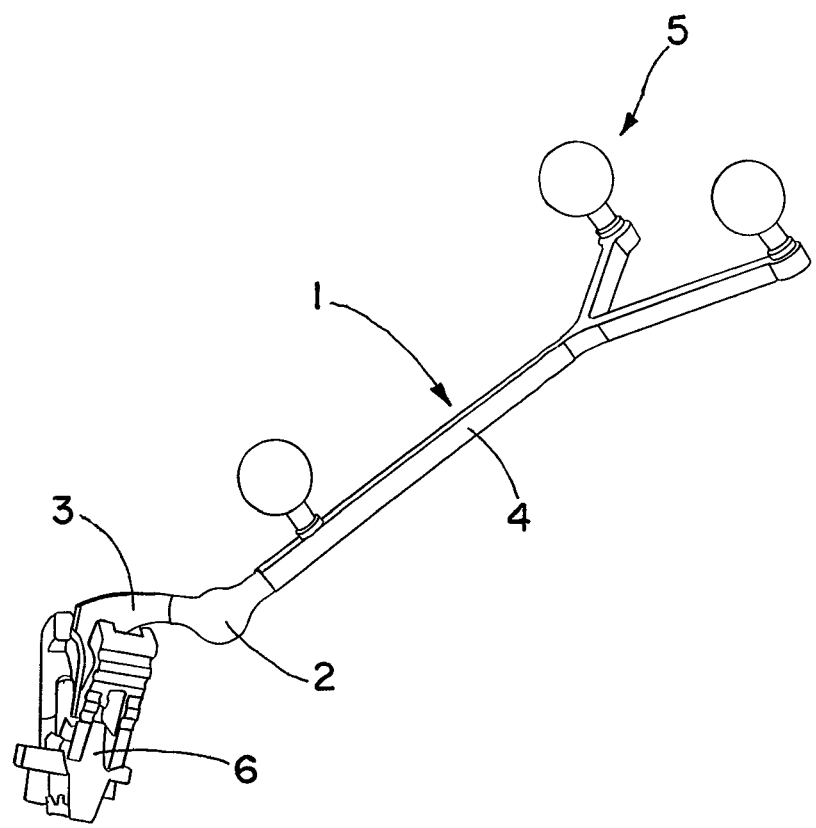
FIG. 1 shows a medical tracking reference in accordance with the present invention.

A medical tracking reference is shown in FIG. 1 and provided with the reference sign 1. It comprises a joint 2 which lies between a fastening arm 3 and a reference array holding arm 4. The fastening arm 3 is so called because the fastening 6 is attached to it, using which the tracking reference 1 can be attached to an object, i.e. for example to a bone, in order to be able to track the bone. The reference array holding arm 4 is so called because the reference array can be attached to it, which in this case consists of three reflective spherical markers, one of which has been provided with the reference sign 5.

The holding arm 4 can be moved relative to the fastening arm 3 by movement in the joint 2, and the angular setting for the holding arm 4 can thus be optimally selected, i.e. such that the reflector markers 5 can directly be detected by a tracking system (free "line of sight").

Figure 2:
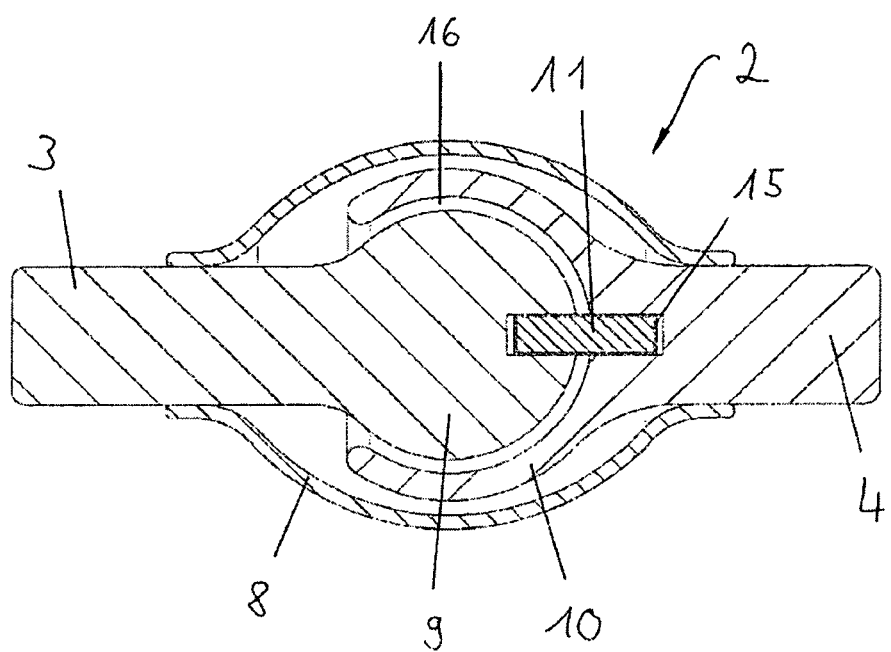
FIG. 2 shows a section through a joint in accordance with a first embodiment of the invention.

One embodiment of a joint is shown in the section in FIG. 2, wherein the joint 2 is designed as a ball joint. The joint 2 comprises the spherical end 9 of the fastening arm 3 and the shell end 10 of the reference array holding arm 4. A covering 8 is attached over the ball joint, terminates at the arms 3, 4 in a seal and is formed from a flexible material. There is a slight clearance between the shell 10 and the sphere 9, i.e. a joint gap 16 is formed there, which may also be referred to as a bonding gap 16. A container 15 is arranged between the front-facing end of the sphere 9 and the deepest point on the shell 10, in cavities in each of these two elements, and comprises a fragile sleeve (glass, plastic) and accommodates the bonding agent 11, for example a one-component glue.

In the state shown in FIG. 2—the initial state—the container 15 can give the joints a certain stability in this position, i.e. the initial position is maintained as long as a larger force is not applied to the joint placement. If, however, the joint is indeed deliberately moved by a somewhat larger force into a particular placement which deviates from the initial placement, the container 15 is destroyed and the bonding agent (glue) 11 can enter the joint gap 16, where it will cure after a short period of time and so fix the desired placement of the joint. This placement can then no longer be altered by inadvertently touching the reference 1, and there is also no danger of forgetting to fix the joint placement because this simply occurs automatically by curing the bonding agent.

Figure 3:
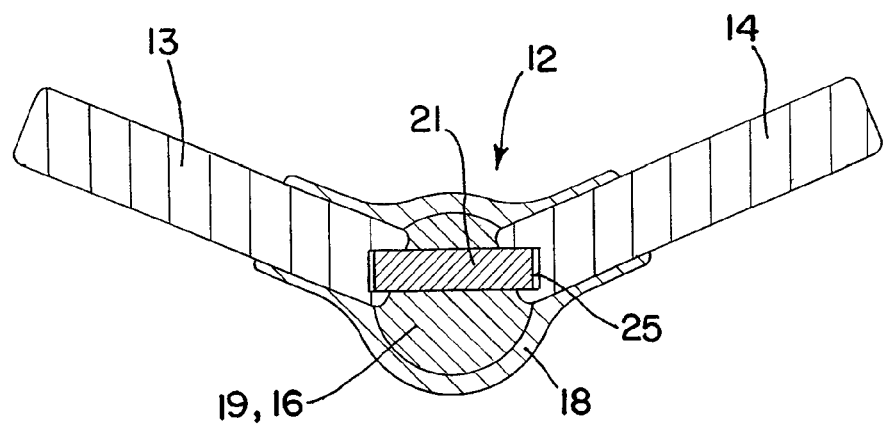
FIG. 3 shows a section through a joint in accordance with a second embodiment of the invention.

Another embodiment of a joint which can be used is shown in the section in FIG. 3; the joint has the reference sign 12 and the two arms are designated as 13 and 14. The joint is again surrounded by a covering 18 which forms a seal on the arms 13, 14, and a component 19 of a bonding agent or glue is situated within the covering 18 in the bonding space 16. The container 25 is stored between the front-facing ends of the arms 13, 14—again in cavities—and in turn comprises the second component 21 of the two-component bonding agent 19, 21. As in the embodiment according to FIG. 2, the container 25 is destroyed when the two arms 13, 14 are moved—for example, placed into their end position; the two components 19, 21 of the bonding agent are mixed and cured, and they then fix the front-facing ends of the arms 13, 14 in the joint, such that said end position is no longer altered.

Figure 4:
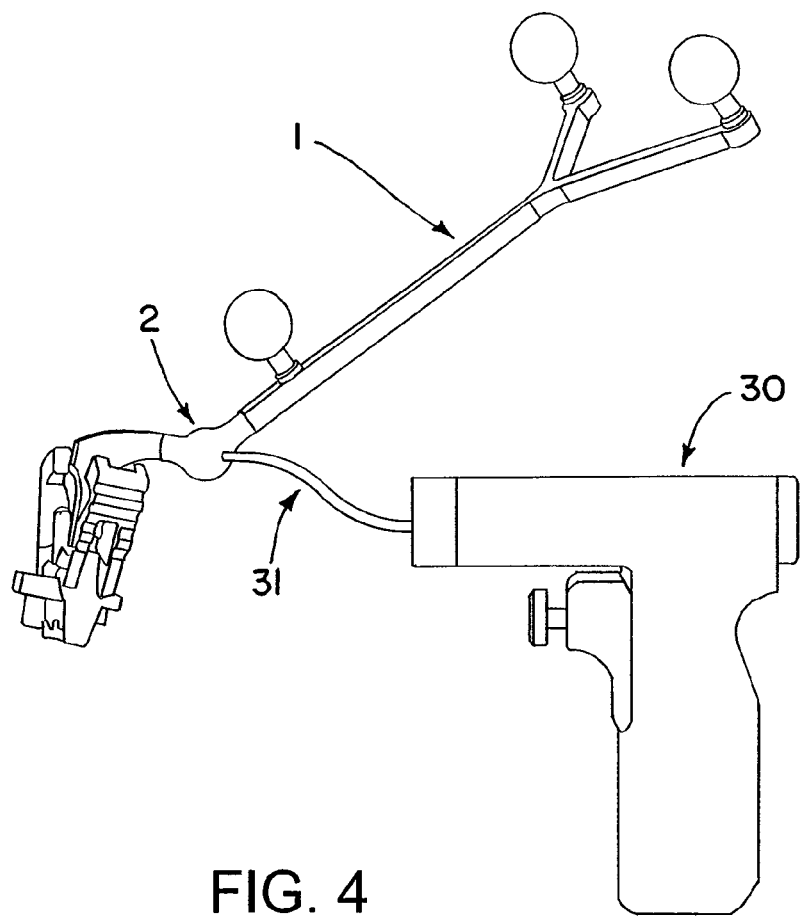
FIG. 4 shows a schematic representation of applying energy to the reference joint in order to change the phase (loose and/or liquid to solid) of the bonding agent.

FIG. 4 shows the tracking reference 1 and an ultrasound emitting device 30, wherein the connection 31 is intended to indicate that said ultrasound device can emit its waves towards the joint. This can illustrate the following two situations:

1. Curing with ultrasound waves: it is possible to cure a bonding agent situated in the bonding space in the joint, using the energy of the ultrasound emitter 30, if the arms have been moved into the desired position beforehand, i.e. this would be an embodiment of the invention in which an ultrasound-curing bonding agent (for example, a one-component bonding agent) is used in the bonding space of the joint 2 and can be easily be cured.

2. Softening (releasing) the joint: conversely, FIG. 4 could also show how a joint which has already been set once beforehand is re-softened by means of an ultrasound emission, i.e. for example, a solidified bonding agent in the bonding space is re-liquefied, such that a new setting can be selected. A very simple example of this would also be a mass which can be plastified by heat and is used as the bonding agent. In its cold state, the joint would be fixedly set; it would be released by the application of heat (for example, microwaves), and when allowed to cool again afterwards, would fix the joint again.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electromagnetic, infrared or semiconductor system, apparatus, device or medium of propagation such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments.

Although the invention has been shown and described with respect to one or more particular preferred embodiments, it is clear that equivalent amendments or modifications will occur to the person skilled in the art when reading and interpreting the text and enclosed drawings of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment or embodiments illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A medical tracking reference, comprising:
 a fastening arm;
 a trackable reference array which is usable to determine, by means of a medical tracking system, the spatial position of an object to which the medical tracking reference is fastened;
 a reference array holding arm to which the trackable reference array is attached;
 a joint arranged between the fastening arm and the reference array holding arm to enable relative movement between the fastening arm and the reference array holding arm, said joint including a curable bonding agent operative to inhibit movement of the joint,
 wherein the joint comprises a bonding space between ends of the respective arms, the bonding space configured to accommodate the bonding agent; and
 a container arranged in or adjacent to the bonding space, wherein the bonding agent is arranged in the container, the container configured to release the bonding agent into the bonding space upon application of a force to the joint.

2. The medical tracking reference according to claim 1, wherein the bonding space is a bonding gap.

3. The medical tracking reference according to claim 1, wherein the bonding space is filled with the curable bonding agent.

4. The medical tracking reference according to claim 3, wherein the curable bonding agent is configured to be cured by introducing a chemical substance or by applying external energy.

5. The medical tracking reference according to claim 4, wherein energy is applied in the form of heating and/or cooling energy, sonic energy, electromagnetic radiation energy or light energy.

6. The medical tracking reference according to claim 1, wherein relative movement of the respective arms releases the bonding agent from the container.

7. The medical tracking reference according to claim 1, wherein when the container is in an unopened state, the container mechanically couples the ends of the arms to each other in the joint to inhibit movement of the arms relative to each other.

8. The medical tracking reference according to claim 1, wherein the bonding agent is a one-component agent which cures in the bonding space after a predetermined period of time.

9. The medical tracking reference according to claim 8, wherein the one-component agent is a one-component glue.

10. The medical tracking reference according to claim 1, wherein the bonding agent is a multiple-component agent which cures after a predetermined period of time due to contact between the multiple components.

11. The medical tracking reference according to claim 10, wherein the multiple-component agent is a multiple-component glue.

12. The medical tracking reference according to claim 10, wherein one of the components is accommodated in the container and another component is accommodated in the bonding space.

13. The medical tracking reference according to claim 1, wherein the bonding agent is a replastifiable agent.

14. The medical tracking reference according to claim 13, wherein the replastifiable agent is configured to be re-liquefied by an external influence.

15. The medical tracking reference according to claim 14, wherein the replastifiable agent is configured to be re-liquefied by applying energy from a location external to the joint.

16. The medical tracking reference according to claim 15, wherein the external energy comprises at least one of heating and/or cooling energy, sonic energy, electromagnetic radiation energy or light energy.

17. The medical tracking reference according to claim 1, wherein the medical tracking device is designed as a reusable reference, and the bonding agent is made from a material having hardening and softening capabilities that are not impaired at sterilization temperatures.

18. The medical tracking reference according to claim 17, wherein the sterilization temperatures are temperatures above 100° C.

19. The medical tracking reference according to claim 1, wherein the medical tracking device is designed as a disposable reference.

20. The medical tracking reference according to claim 19, wherein the arms and the joint are made from a plastic material, and/or the bonding agent is made from a material which irretrievably loses its strength and/or solidity at sterilization temperatures.

21. The medical tracking reference according to claim 20, wherein the sterilization temperatures are temperatures above 100° C.

22. The medical tracking reference according to claim 1, wherein the joint comprises a flexible sleeve which ends at the arms and creates a seal at each arm.

23. The medical tracking reference according to claim 1, wherein the joint comprises a ball joint.

24. A medical tracking reference, comprising:
a fastening arm;
a reference array holding arm to which a trackable reference array is or can be attached; and
a joint arranged between the fastening arm and the reference array holding arm to enable relative movement between the fastening arm and the reference array holding arm, wherein the joint comprises a container arranged in or adjacent to a bonding space, and application of a predetermined force on the joint opens the container.

* * * * *